(12) United States Patent
Taguchi et al.

(10) Patent No.: US 7,468,162 B2
(45) Date of Patent: Dec. 23, 2008

(54) ANALYTICAL INSTRUMENT

(75) Inventors: Takayuki Taguchi, Kyoto (JP); Shigeru Kitamura, Kyoto (JP)

(73) Assignee: Arkray, Inc., Kyoto (JP)

( * ) Notice: Subject to any disclaimer, the term of this patent is extended or adjusted under 35 U.S.C. 154(b) by 789 days.

(21) Appl. No.: 10/513,862

(22) PCT Filed: Apr. 28, 2003

(86) PCT No.: PCT/JP03/05479

§ 371 (c)(1),
(2), (4) Date: Oct. 29, 2004

(87) PCT Pub. No.: WO03/093834

PCT Pub. Date: Nov. 13, 2003

(65) Prior Publication Data

US 2005/0201892 A1    Sep. 15, 2005

(30) Foreign Application Priority Data

Apr. 30, 2002    (JP)    ............................. 2002-128950

(51) Int. Cl.
*B01L 3/02* (2006.01)
(52) U.S. Cl. ..................................................... 422/100
(58) Field of Classification Search ................. 422/100
See application file for complete search history.

(56) References Cited

U.S. PATENT DOCUMENTS

| 5,595,712 | A | 1/1997 | Harbster et al. |
| 6,126,765 | A * | 10/2000 | Ohman .................. 156/74 |
| 6,167,910 | B1 * | 1/2001 | Chow .................. 137/827 |
| 6,176,962 | B1 | 1/2001 | Soane et al. |
| 6,197,494 | B1 | 3/2001 | Oberhardt |
| 6,334,301 | B1 * | 1/2002 | Otsap et al. ............ 60/200.1 |
| 2002/0023684 | A1 | 2/2002 | Chow |
| 2002/0029814 | A1 | 3/2002 | Unger et al. |

FOREIGN PATENT DOCUMENTS

| EP | 0 359 831 | 3/1990 |
| JP | 1-291153 | 11/1989 |
| JP | 2001-304440 | 10/2001 |
| JP | 2002-48752 | 2/2002 |
| WO | WO 98/45693 | 10/1998 |

OTHER PUBLICATIONS

Shoji, *Chemistry*, vol. 54, No. 10, pp. 36-38 (1999).

* cited by examiner

*Primary Examiner*—Walter D Griffin
*Assistant Examiner*—Bobby Ramdhanie
(74) *Attorney, Agent, or Firm*—Hamre, Schumann, Mueller & Larson, P.C.

(57) ABSTRACT

An analytical instrument (A1) includes a capillary (3) defined by causing a first member (1) to cover an opening of a groove (30) of a second member (2). For bonding the first member (1) and the second member (2), the first member (1) is provided with a bonding surface (11a) made of self-adherent elastomer. Therefore, the bonding of the first member (1) and the second member (2) is facilitated, whereby sealing performance around the groove (30) is improved.

7 Claims, 9 Drawing Sheets

ANALYTICAL INSTRUMENT

TECHNICAL FIELD

The present invention relates to an analytical instrument used for analyzing a sample in a liquid state such as a body fluid.

BACKGROUND ART

FIGS. 11A and 11B show an example of prior art analytical instrument. The analytical instrument includes a substrate 90 and a cover 91 stacked and bonded together to define a capillary 92. The capillary 92 is defined by closing an upper opening of a groove 92a formed at an upper surface of the substrate 90 by the cover 91. In the analytical instrument, when a sample in a liquid state is supplied to a sample introduction port 93 formed in the cover 91, the sample travels through the capillary 92 in a direction indicated by the arrow Na by capillary action. While the sample travels through the capillary 92, the sample may be mixed with a reagent for causing a predetermined reaction or subjected to component separation, whereby the sample is analyzed.

Conventionally, the substrate 90 and the cover 91 have sometimes been made of glass or silicone. In such a case, the substrate 90 and the cover 91 can be reliably bonded together by water glass bonding or anode bonding, for example. However, since the working of glass or silicone is not easy, the cost for manufacturing the analytical instrument disadvantageously increases.

In recent years, therefore, the substrate 90 and the cover 91 are often made of a synthetic resin for decreasing the cost for the parts. In such a case, the substrate 90 and the cover 91 are often bonded together with an adhesive or by fusing utilizing ultrasonic wave.

However, such a prior art structure has the following problems.

First, it is difficult to form a capillary 92 of an intended size. As shown in FIG. 12, when the substrate 90 and the cover 91 are bonded together with an adhesive 80, the vertical dimension H of the capillary 92 (the dimension in the thickness direction of the analytical instrument) becomes the total dimension of the depth h1 of the groove 92a and the thickness h2 of the adhesive 80. However, it is difficult to apply the adhesive 80 uniformly into a predetermined thickness. Therefore, due to the variation of the thickness of the adhesive 80, the capillary 92 having an intended vertical dimension sometimes cannot be formed. In the case where ultrasonic wave is utilized, a projection in the form of a rib (not shown) is formed at a bonding surface, and ultrasonic wave is applied to the projection to heat and deform the projection. At this time, the portion to be deformed vibrates at an amplitude of about 10 μm. Due to such vibration, the degree of deformation of the projection cannot be kept constant, so that the capillary 92 of an intended size may not be formed. When the size of the capillary 92 differs from an intended, proper one, conditions such as the travel speed or amount of the sample which flows through the capillary 92 may differ from the intended conditions, which may cause inaccurate analysis results.

Secondly, the manufacturing of the analytical instrument is difficult when the configuration of the capillary 92 is complicated. In applying the adhesive 80 to the substrate 90, the groove 92a need be avoided so that the adhesive 80 does not enter the groove 92a. Therefore, when the configuration of the capillary 92 is complicated, the application of the adhesive following the configuration is troublesome and difficult.

When ultrasonic wave is utilized, the projection for fusing need be formed correspondingly to the configuration of the capillary 92. Therefore, in such a case again, the work is troublesome when the configuration of the capillary 92 is complicated.

Thirdly, the sealing performance around the capillary 92 is not good. For example, when the adhesive is not applied to a portion of the edge of the groove 92a in applying the adhesive 80 to the substrate 90, the portion forms a gap communicating with the capillary 92, causing a fear that the sample may unduly enter the portion. Such a fear exists also when ultrasonic wave is utilized. Particularly when the substrate 90 and the cover 91 are molded of resin, these members are sometimes warped to reduce the flatness at the bonding surfaces. In such a case, the sealing performance around the capillary 92 is further deteriorated.

In recent years, studies are performed to reduce the size of an entire chemical analysis system by reducing the size of the structural parts of the system and integrating the parts. When the size of the chemical analysis system is reduced, the price of the system can be reduced. Further, since the analysis can be performed by using a smaller amount of sample, it is possible to reduce the time required for the analysis, the power consumption for actuating the system, and the amount of liquid wasted after the analysis. To reduce the size of the analytical instrument to follow the downsizing trend of the chemical analysis system, a considerably small capillary 92 having a precisely intended size need be formed. However, it is difficult to meet such need when the substrate 90 and the cover 91 are bonded together with an adhesive or by utilizing ultrasonic wave.

DISCLOSURE OF THE INVENTION

An object of the present invention is to provide an analytical instrument capable of solving or lessening the above-described problems.

According to a first aspect of the present invention, there is provided an analytical instrument comprising a first and a second members stacked on each other, and a capillary defined by covering an opening of a groove formed in one of the first and the second members with the other of the first and the second members. The first member includes a bonding surface made of self-adherent elastomer, and the first and second members are bonded together via the bonding surface.

Preferably, the first member comprises a non-adherent base member and a sheet of self-adherent elastomer bonded to the base member, and the bonding surface comprises one surface of the sheet.

Preferably, the first member is entirely made of self-adherent elastomer.

Preferably, the second member is made of a non-adherent material, and the groove is formed in the second member.

Preferably, the second member comprises a plate or sheet having one surface at which the groove is formed as a bottomed groove, and the first member is bonded to the one surface of the second member.

Preferably, the capillary has one end branching into a plurality of paths, and the paths are formed with a sample receiving portion and a reagent receiving portion connected thereto. The capillary has another end formed with a reaction portion connected thereto for causing reaction between a sample and a reagent.

Preferably, the analytical instrument according to the present invention includes a plurality of second members, and the first member comprises a plate or sheet in which the groove is formed to penetrate thicknesswise and which has an obverse surface and a reverse surface each serving as the bonding surface. The plurality of second members are bonded to the obverse surface and the reverse surface of the first member.

Preferably, the analytical instrument according to the present invention includes a plurality of first members, and the second member comprises a plate or sheet in which the groove is formed to penetrate thicknesswise. The second member has an obverse and a reverse surfaces to which the first members are bonded.

Preferably, the capillary has one end serving as a sample introduction port and includes a reaction portion containing a reagent.

According to a second aspect of the present invention, there is provided an analytical instrument comprising a first and a second members stacked on each other, and a capillary defined by causing the second member to cover an opening of a groove formed in the first member. The second member is made of elastomer, and the analytical instrument further includes a third member for pressing the second member against the first member.

Preferably, the second member is sandwiched between the first and the third members, and the third member is partially bonded to the first member at an outer periphery of the second member.

Preferably, the third member includes a projection for engaging the first member at an outer periphery of the second member, and respective engaging portions of the projection and the first member are bonded together.

Preferably, the third member comprises a flexible plate or sheet, and the third member being flexibly deformed so that an outer periphery of the third member comes into contact with the first member. Respective contacting portions of the third member and the first member are bonded together.

Other features and advantages of the present invention will become clearer from the detailed description given below with reference to the accompanying drawings.

BRIEF DESCRIPTION OF THE DRAWINGS

FIG. 11A is a sectional view showing a prior art structure, whereas

BEST MODE FOR CARRYING OUT THE INVENTION

Preferred embodiments of the present invention will be described below in detail with reference to the accompanying drawings.

Figure 1:
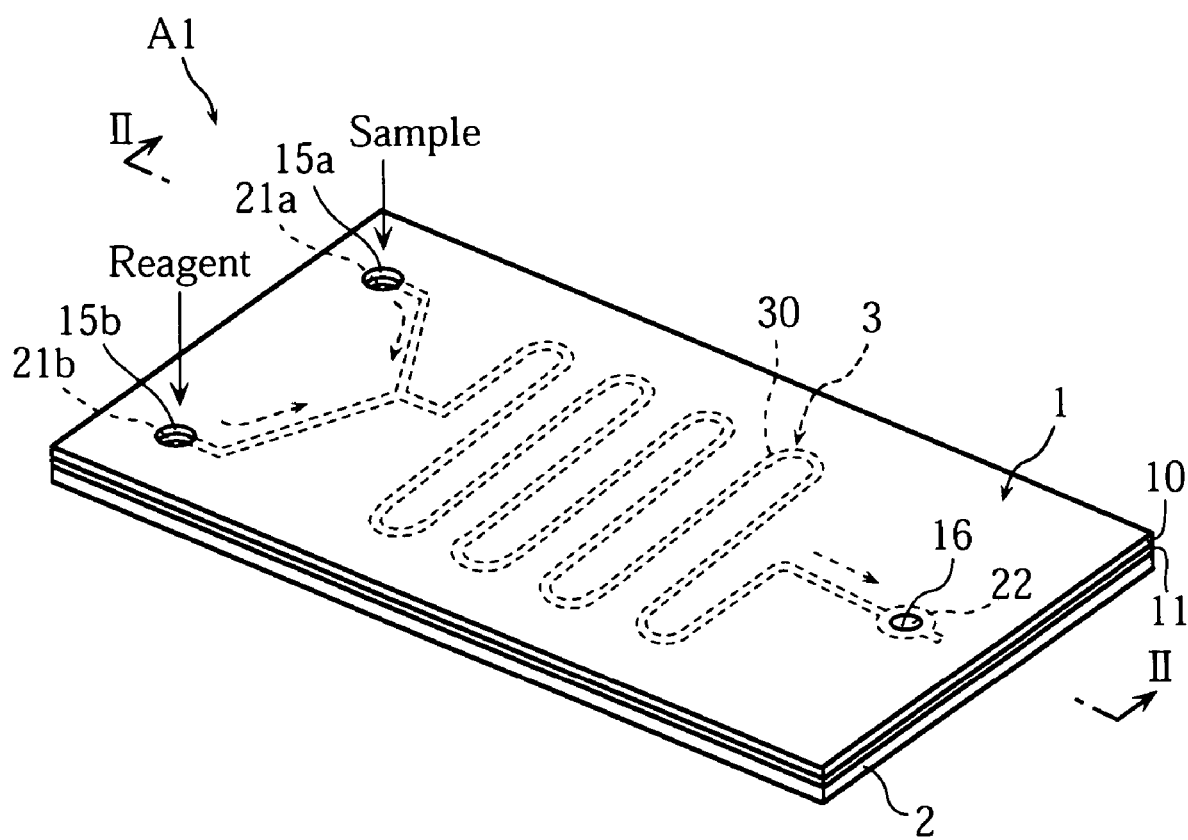
FIG. 1 is a perspective view showing an embodiment of analytical instrument according to the present invention.
Figure 2:
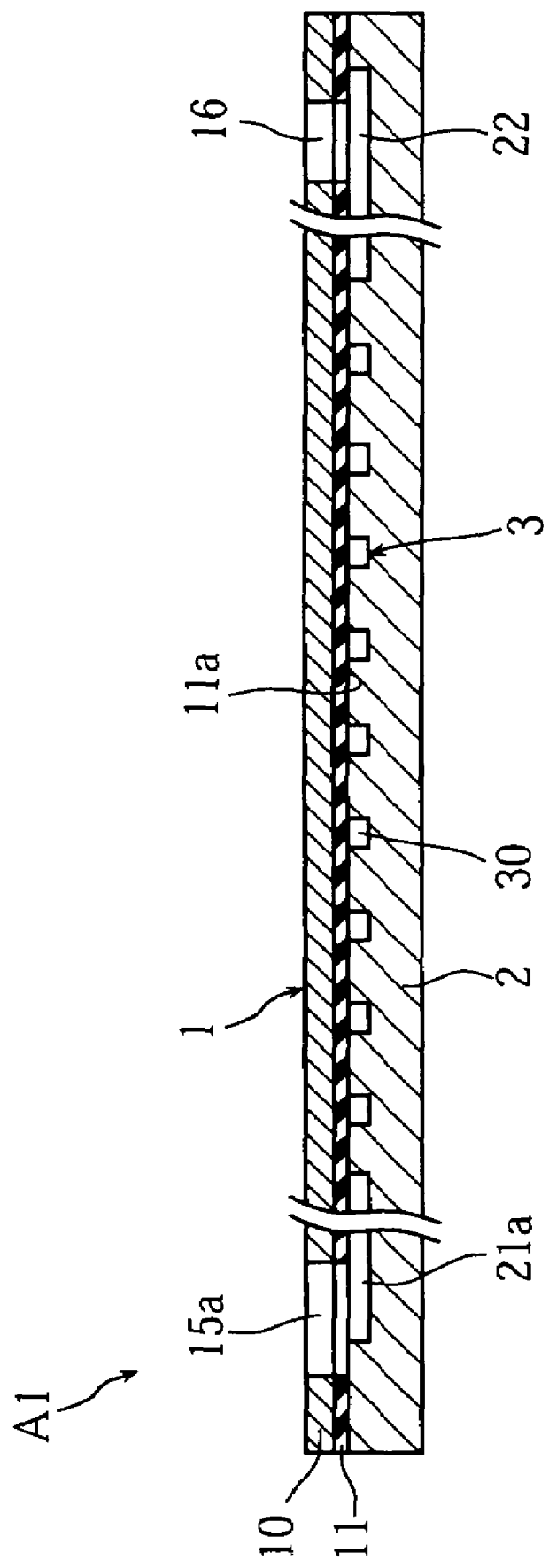
FIG. 2 is a sectional view taken along lines II-II in FIG. 1.
Figure 3:
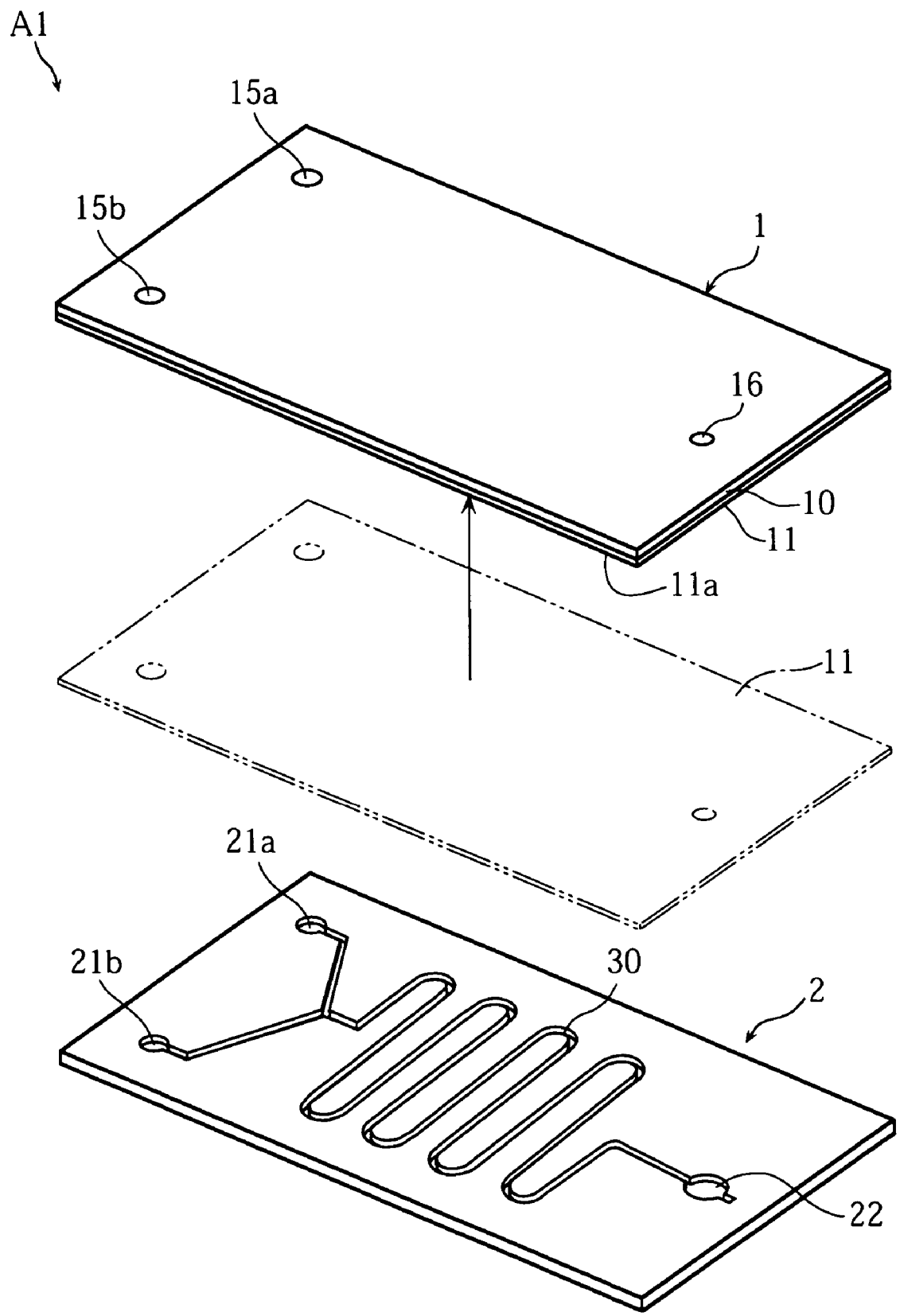
FIG. 3 is an exploded perspective view of the analytical instrument shown in FIG. 1.

FIGS. 1-3 show an embodiment of analytical instrument according to the present invention. The analytical instrument A1 of this embodiment includes a cover 1, a substrate 2 and a capillary 3 provided between the cover and the substrate. The cover 1 and the substrate 2 are examples of a first and a second members of the present invention.

The cover 1 comprises a flexible rectangular plate or sheet formed by laminating a sheet 11 made of a self-adherent elastomer on a base member 10. Specifically, the sheet 11 may be made of silicone rubber. In the present invention, however, the material is not limited to a specific one, and other self-adherent elastomer may be used. However, it is preferable to use an elastomer that does not adversely affect the analysis results of the sample upon contact with the sample. The sheet 11 has opposite surfaces both of which are adherent and is bonded to the base member 10 by utilizing the adhesion of one of the opposite surfaces. The other one of the opposite surfaces serves as a bonding surface 11a for bonding the cover 1 to the substrate 2. The base member 10 is made of a non-adherent synthetic resin.

The substrate 2 comprises a plate or sheet having a rectangular configuration similar to that of the cover 1 and made of a non-adherent synthetic resin. The substrate 2 has an upper surface formed with a narrow bottomed groove 30 serving as the capillary 3. The groove 30 is made serpentine to have a large length for promoting the mixing of a sample with a reagent, which will be described later. The groove 30 has opposite ends one of which is divided into two branches. The two branches are respectively connected to a sample receiving portion 21a and a reagent receiving portion 21b each in the form of a recess. The other end of the groove 30 is connected to a reaction portion 22 in the form of a recess.

The cover 1 is stacked on the substrate 2 so that the bonding surface 11a comes into contact with the upper surface of the substrate 2 and bonded to the substrate 2 due to the adhesion of the bonding surface 11a. The capillary 3 is defined by closing an upper opening of the groove 30 by the cover 1. The cover 1 is formed with a sample introduction port 15a and a reagent introduction port 15b respectively communicating with the sample receiving portion 21a and the reagent receiving portion 21b of the substrate 2, and a measurement opening 16 communicating with the reaction portion 22.

In the analytical instrument A1, when a sample and a reagent in a liquid state is supplied to the sample introduction port 15a and the reagent introduction port 15b, the sample and the reagent travel through the capillary 3 by capillary action to be mixed together and reaches the reaction portion 22 while undergoing certain reaction. The analysis of the sample may be performed by examining the optical characteristics of the liquid mixture of the sample and the reagent having reached the reaction portion 22 through the measurement opening 16 using an optical measuring device (not shown), for example.

The analytical instrument A1 has a structure provided by directly bonding the cover 1 and the substrate 2 to each other by utilizing the adhesion of the bonding surface 11a. Therefore, unlike the case in which the cover and the substrate are bonded together with an adhesive or by utilizing ultrasonic wave, the application of an adhesive to the cover 1 or the substrate 2 or the application of ultrasonic wave is not necessary. Therefore, the work for bonding the cover 1 and the substrate 2 is easy. Although the capillary 3 has a complicated serpentine configuration, the flat bonding surface 11a of the cover 1 need not be worked otherwise. Therefore, the cover 1 can be made easily so that the analytical instrument A1 can be manufactured at a relatively low cost.

As noted above, the analytical instrument A1 is manufactured without using an adhesive. Therefore, unlike the prior art instrument which is made by using an adhesive, variation of the size of the capillary 3 due to the variation of the thickness of the adhesive can be avoided. Therefore, a capillary 3 having just the intended size can be formed, so that the time taken for the sample and the reagent to reach the reaction portion 22 from the sample introduction port 15a and the reagent introduction port 15b or other conditions such as the degree of mixing can be prevented from becoming improper.

In bonding the cover 1 and the substrate 2 together, the bonding surface 11a of the cover 1 can be closely fitted to the generally entire region of the upper surface of the substrate 2 (except for the intentionally recessed portion such as the portion formed with the groove 30). Therefore, the bonding strength of the cover 1 and the substrate 2 can be enhanced. Moreover, the cover 1 can be reliably bonded also to the edges of the grove 30, whereby sealing performance at the periphery of the capillary 3 can be enhanced. Even when the upper surface of the substrate 2 is curved due to the warp of the substrate 2, the cover 1 can be closely fitted to the substrate 2 by flexing the cover 1 correspondingly.

Figure 4:
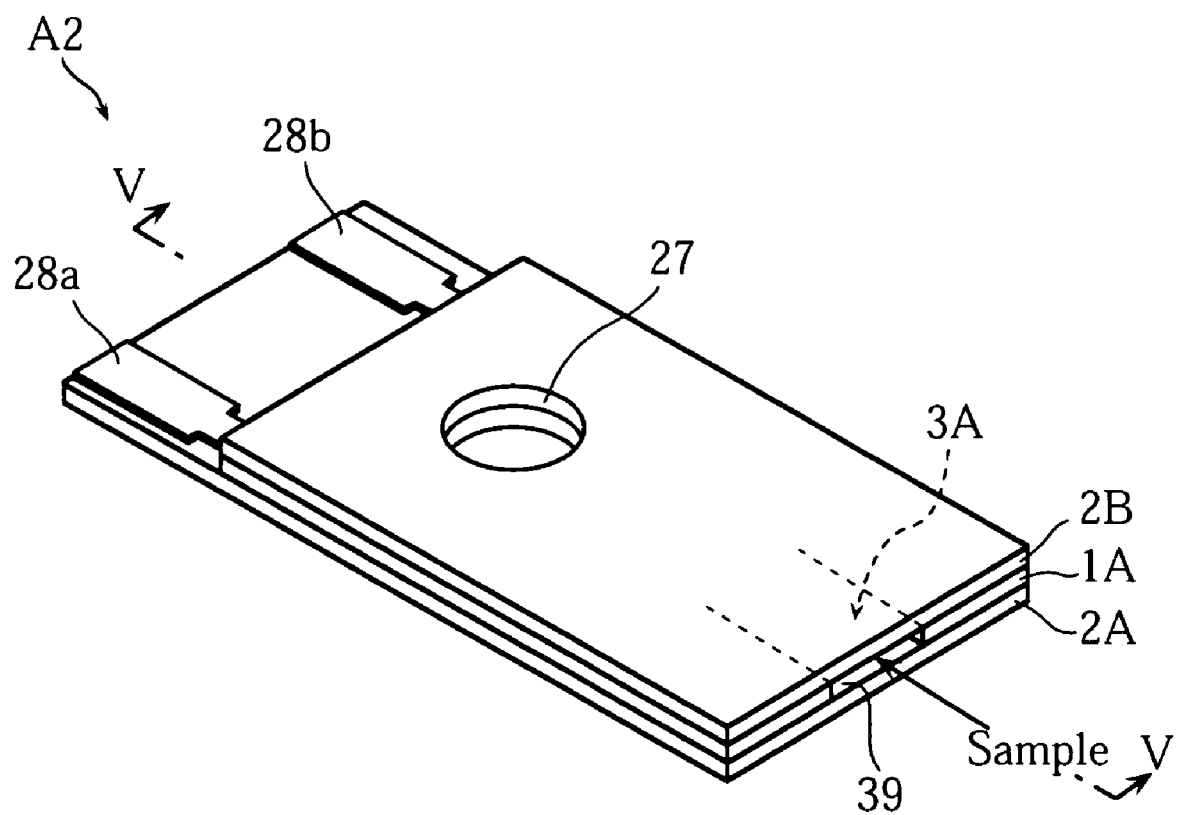
FIG. 4 is a perspective view showing another embodiment of analytical instrument according to the present invention.
Figure 5:
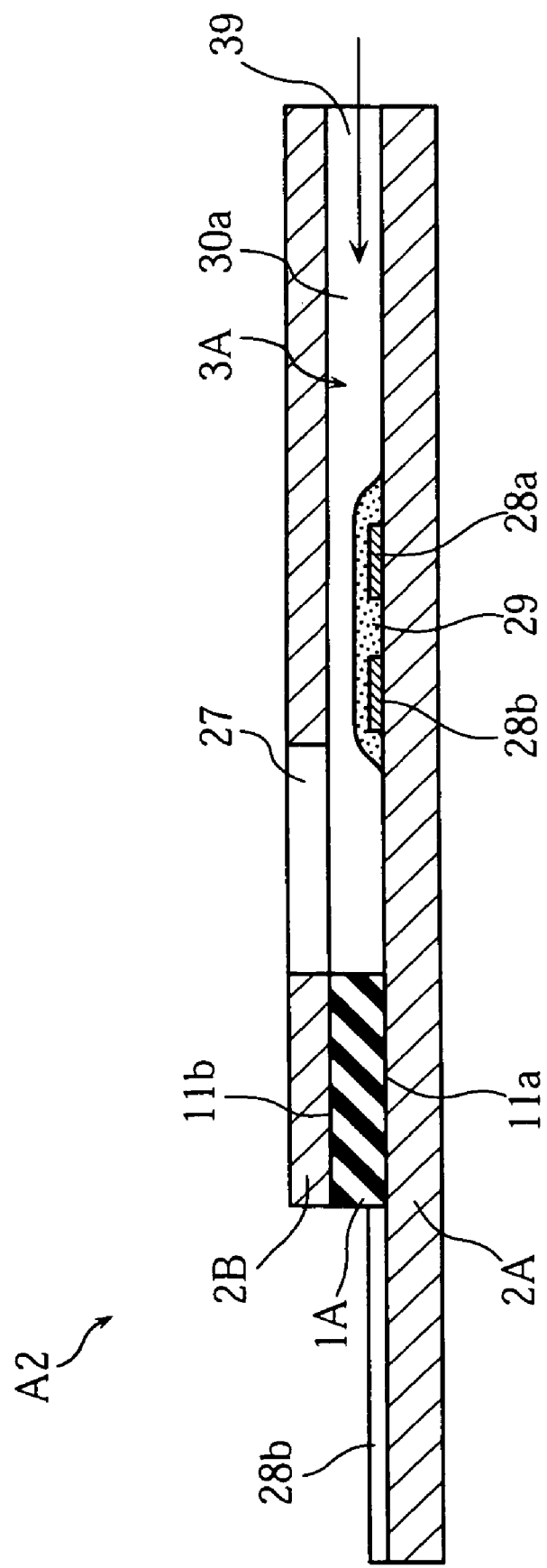
FIG. 5 is a sectional view taken along lines V-V in FIG. 4.
Figure 6:
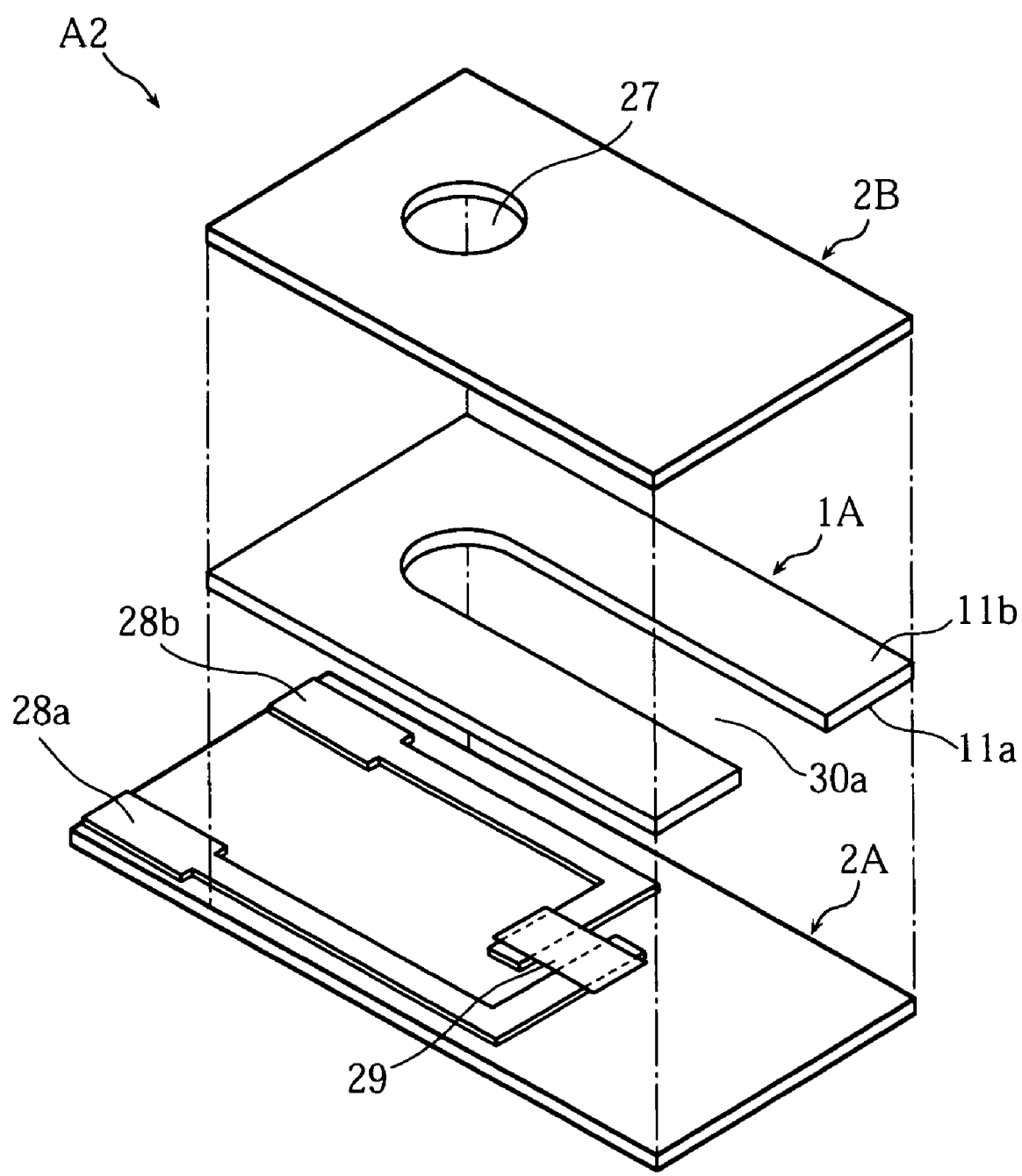
FIG. 6 is an exploded perspective view of the analytical instrument shown in FIG. 4.

FIGS. 4-7 illustrate another embodiment of analytical instrument according to the present invention. In FIG. 4 and the subsequent figures, the elements which are identical or similar to those of the foregoing embodiment are designated by the same reference signs as those used for the foregoing embodiment.

The analytical instrument A2 of this embodiment includes a spacer 1A, a substrate 2A and a cover 2B. The spacer 1A is an example of first member of the present invention, whereas the substrate 2A and the cover 2B are examples of second member of the present invention.

Figure 7:
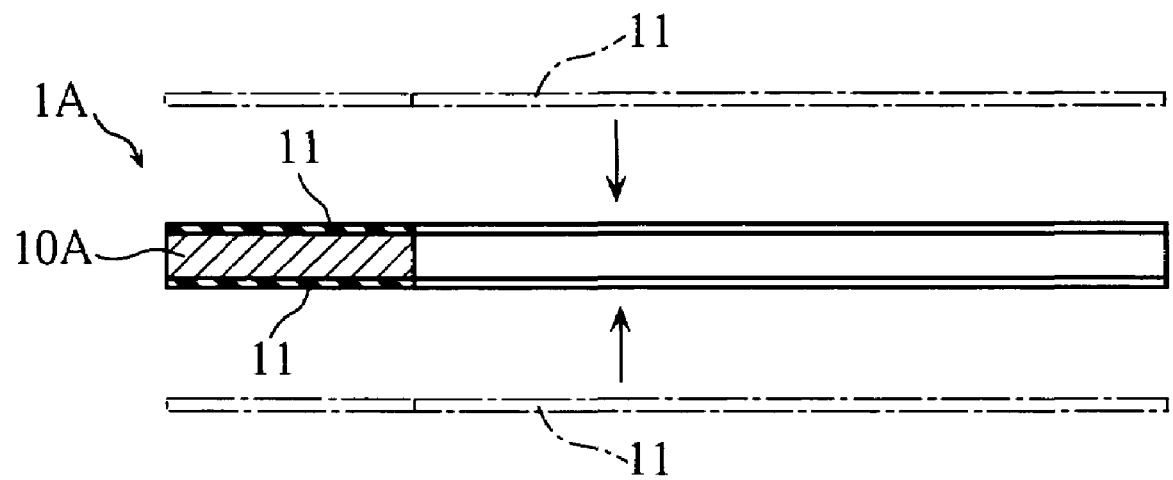
FIG. 7 is a sectional view showing another example of spacer of the analytical instrument shown in FIG. 4.

The spacer 1A comprises a flexible plate or sheet formed with a groove 30a penetrating thicknesswise for constituting a capillary 3A. The spacer 1A has an upper and a lower surfaces serving as bonding surfaces 11a, 11b made of self-adherent elastomer. To make the upper and the lower surfaces of the spacer 1A bonding surfaces 11a, 11b, the entirety of the spacer 1A may be made of self-adherent elastomer. In such a case, the spacer 1A can be manufactured easily. Alternatively, as shown in FIG. 7, a pair of sheets 11 made of self-adherent elastomer may be bonded to an upper and a lower surfaces of a non-adherent base member 10A.

Both of the substrate 2A and the cover 2B comprise a generally rectangular plate or sheet made of a non-adherent synthetic resin. The substrate 2A has an upper surface formed with a reaction portion 29 including a reagent, and a pair of electrodes 28a, 28b. The cover 2B is formed with a hole 27 for discharging air from the capillary 3A.

The substrate 2A and the cover 2B are stacked to sandwich the spacer 1A in the thickness direction and bonded to the spacer 1A due to the adhesion of the bonding surfaces 11a, 11b of the spacer 1A. The upper and lower openings of the groove 30a of the spacer 1A is closed by the substrate 2A and the cover 2B, whereby the capillary 3A is defined. One end of the capillary 3A is open at an end surface of the analytical instrument 2A, and the opening serves as a sample introduction port 39.

In the analytical instrument A2, when a sample in a liquid state is supplied to the sample introduction port 39, the sample moves through the capillary 3A by capillary action and undergoes certain reaction upon reaching the reaction portion 29. For example, the concentration of a particular component in the sample can be measured by electrically detecting the degree of reaction by using a pair of electrodes 28a, 28b. Although such measurement principle is typically applicable to the measurement of a glucose level in blood, it is also applicable to concentration measurement of other components by changing the kind of the reagent in the reaction portion 29, for example.

In the analytical instrument A2, the substrate 2A and the cover 2B are directly bonded to the spacer 1A by utilizing adhesion of the bonding surfaces 11a, 11b. Therefore, similarly to the above analytical instrument A1, the bonding can be performed easily. Further, a capillary 3A of an intended size can be reliably formed. Therefore, the analytical instrument A2 does not suffer from such a problem that the amount of the sample reaching the reaction portion 29 becomes excessive or insufficient due to the improper size of the capillary 3A. In the analytical instrument A2, the entirety of the bonding surfaces 11a, 11b of the spacer 1A can be closely fitted to the substrate 2A and the cover 2B, respectively. Therefore, the same advantages as those of the analytical instrument A1, such as improved sealing performance at the periphery of the capillary 3A, can be obtained.

The present invention is not limited to the foregoing embodiments. Specific structure of each component of the analytical instrument according to the present invention may be modified in various ways.

Figure 8:
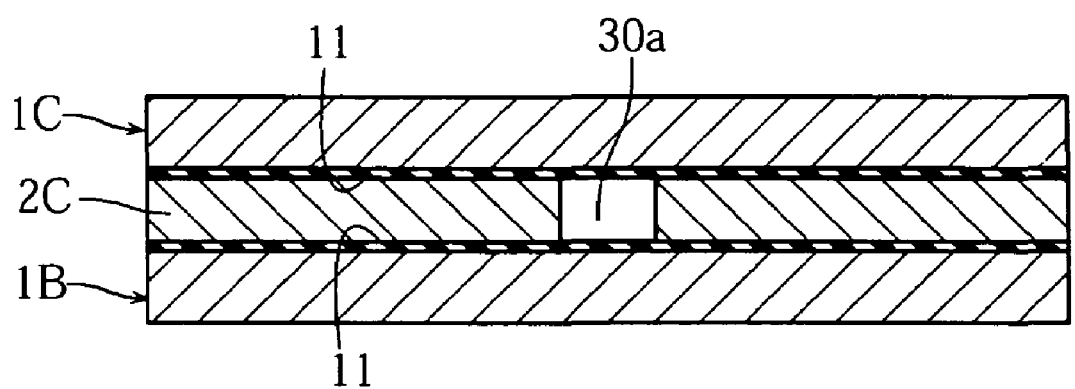
FIG. 8 is a sectional view showing another embodiment of analytical instrument according to the present invention.

In the structure shown in FIG. 8, upper and lower surfaces of the spacer 2C formed with a groove 30a are not self-adherent, and each of the substrate 1B and the cover 1C has a self-adherent bonding surface 11. In other words, in this structure, the second member is sandwiched between two first members each of which is provided with a bonding surface made of self-adherent elastomer. The present invention can also employ such a structure.

The present invention is applicable to any analytical instrument which includes at least two members bonded together and a capillary provided between the members, and the kind and components of the substance to be analyzed is not limitative. The manner of using the analytical instrument is not limitative. The specific configuration and the like of the first and the second members in the present invention may be appropriately changed in accordance with the usage. In the present invention, both of the first and the second members may have self-adherent bonding surfaces. As will be understood from the above description, the groove for constituting the capillary may be formed in either of the first member and the second member.

The present invention is applicable also when the structural component of the analytical instrument is not made of a synthetic resin. A self-adherent elastomer exhibits a good adhesion also to glass, for example. Therefore, the present invention is applicable also when part of the structural component of the analytical instrument is made of e.g. glass and provides intended advantages.

Figure 9:
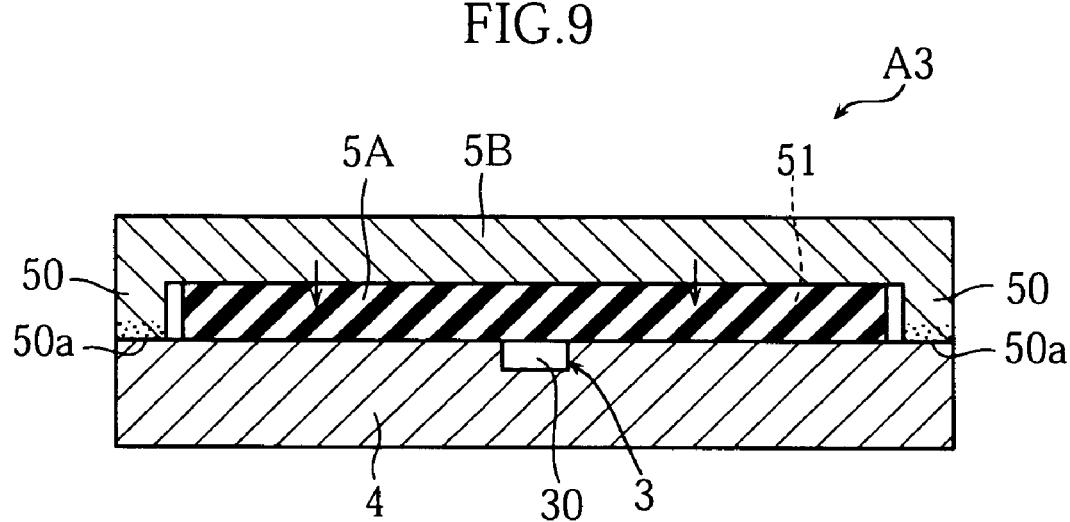
FIG. 9 is a sectional view showing another embodiment of analytical instrument according to the present invention.

FIG. 9 shows another embodiment of the present invention.

The analytical instrument A3 of this embodiment includes a substrate 4, and a first and a second covers 5A, 5B. All of these structural components are non-adherent, and the analytical instrument A3 differs from the foregoing embodiments in that a self-adherent component is not used. The substrate 4 is an example of the first member of the present invention, whereas the first and the second covers 5A, 5B are examples of the second and the third members of the present invention.

The substrate 4 comprises e.g. a rectangular plate or sheet made of a synthetic resin and has an upper surface formed with a bottomed groove 30 for constituting a capillary 3. The first cover 5A is made of an elastomer having an elastic modulus (modulus of elasticity) that is lower than those of the substrate 4 and the second cover 5B. Specific examples of material of the first cover 5A include polyvinylidene chloride and ethylene propylene rubber, but the material is not limited to these. The first cover 5A is in the form of a rectangular sheet slightly smaller than the substrate 4 and stacked on the upper surface of the substrate 4.

The second cover 5B is in the form of a generally rectangular plate or sheet of a size which is larger than that of the first cover 5A and formed with a downwardly extending projection 50 at the entirety or almost entirety of the outer periphery. The second cover 5B covers the first cover 5A to accommodate the first cover 5A in a space 51 surrounded by the projection 50. The projection has a front end 50a (lower end) fused to the upper surface of the substrate 4. In the fusing, the second cover 5B compress the first cover 5A appropriately in the thickness direction.

The analytical instrument A3 of this embodiment includes a capillary 3 defined by covering an upper opening of the groove 30 by the first cover 5A. To manufacture the analytical instrument A3, the first cover 5A need not be bonded to the substrate 4 with an adhesive. The analytical instrument can be made by stacking the first and the second covers 5A, 5B on the substrate 4 and then fusing the outer periphery of the second cover 5B to the substrate 4 by heating utilizing a heater or ultrasonic wave. Therefore, the work is easy. Since the fusion of the second cover 5B and the substrate 4 is performed at a location away from the capillary 3, the fusing operation does not adversely affect the formation of the capillary 3.

Since the first cover 5A is made of an elastomer and appropriately compressed by the pressing force of the second cover 5B, the first cover 5A closely fits to the upper surface of the substrate 4. Even when the substrate 4 is slightly warped, the first cover 5A is deformed correspondingly to the warp, so that the first cover 5A can be closely fitted to the substrate 4. Therefore, good sealing performance is provided at the periphery of the capillary 3. The first cover 5A is prevented from floating above the substrate 4. Therefore, the vertical dimension of the capillary 3 can be set precisely to an intended one.

Figure 10:
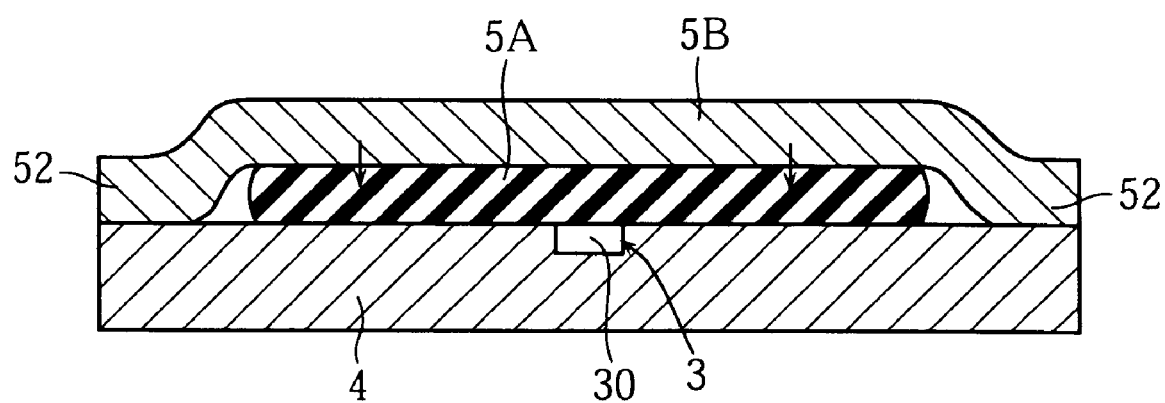
FIG. 10 is a sectional view showing another embodiment of analytical instrument according to the present invention.
Figure 11A:
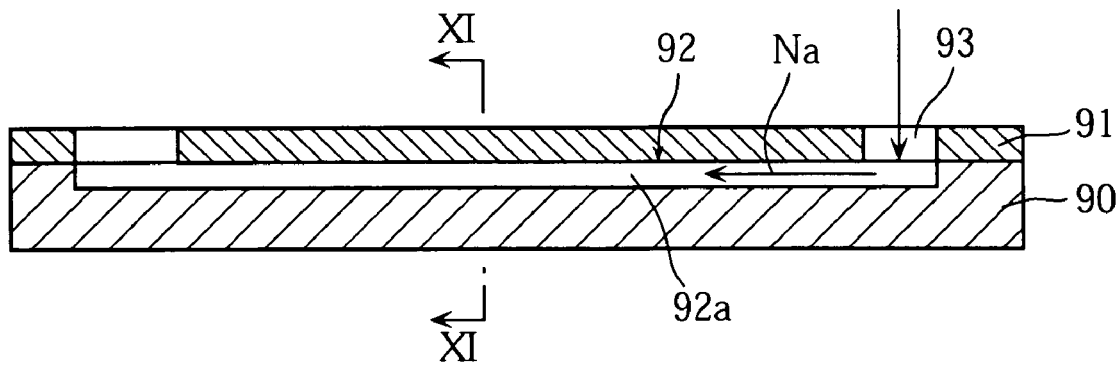
Figure 11B:
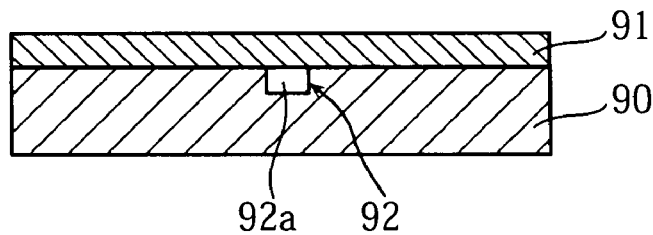
FIG. 11B is a sectional view taken along lines XI-XI in FIG. 11A.
Figure 12:
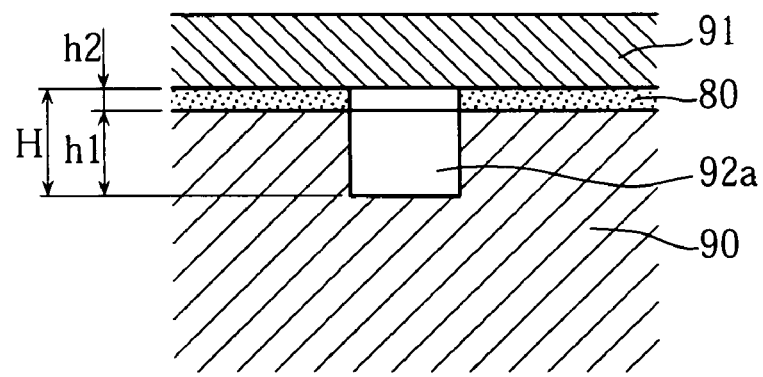
FIG. 12 is an enlarged sectional view showing a principal portion of the prior art structure.

Like the above embodiment, the analytical instrument according to the present invention can have a structure using a non-adherent elastomer. The second cover 5B may comprise a flexible plate or sheet which is not provided with the projection 50. For example, as shown in FIG. 10, the portion 52 of the second cover 5B, which projects outward to the periphery of the first cover 5A, may be laid on the substrate 4 and fused to the substrate. In such a case again, the first cover 5A can be pressed against the upper surface of the substrate 4 by the second cover 5B, whereby the same advantages as those of the analytical instrument A3 can be obtained. The means for bonding the second cover 5B to the substrate 4 is not limited to fusing, and an adhesive may be used. In bonding the second cover 5B to the substrate 4 with an adhesive, the adhesive is applied to the outer edges of the second cover 5B or the corresponding portion of the substrate 4. Unlike the prior art instrument, the adhesive need not be applied to the nearby portion of the capillary, so that the application is easy.

As shown in FIGS. 9 and 10, also in the analytical instrument of the present invention which utilizes a non-adherent elastomer, the specific structure can be modified in various ways. For example, the configuration of the substrate is not limited to the form of a sheet or plate.

The invention claimed is:

1. An analytical instrument comprising:
   a substrate formed with a groove;
   a first cover made of elastomer and stacked on the substrate covering the groove and defining a capillary; and
   a second cover covering the first cover;
   wherein the second cover includes an outer periphery located outward of the first cover and bonded directly to the substrate.

2. The analytical instrument according to claim 1, wherein the outer periphery of the second cover has a projection projecting toward the substrate and bonded thereto.

3. The analytical instrument according to claim 2, wherein the projection surrounds the first cover.

4. The analytical instrument according to claim 1, wherein the second cover comprises a flexible plate or sheet, the second cover being flexibly deformed so that the outer periphery of the second cover projects outward and comes into bonding contact with the substrate.

5. The analytical instrument according to claim 1, wherein the first cover is sandwiched between the substrate and the second cover in a compressed state.

6. The analytical instrument according to claim 1, wherein the elastomer for the first cover is non-adherent.

7. The analytical instrument according to claim 6, wherein the elastomer for the first cover is polyvinylidene chloride or ethylene propylene rubber.

* * * * *